United States Patent [19]

Wong

[11] Patent Number: 4,457,934

[45] Date of Patent: * Jul. 3, 1984

[54] INSECT REPELLENT COMPOUNDS

[75] Inventor: Rayman Y. Wong, Richmond, Calif.

[73] Assignee: Stauffer Chemical Company, Westport, Conn.

[*] Notice: The portion of the term of this patent subsequent to Sep. 7, 1999 has been disclaimed.

[21] Appl. No.: 404,245

[22] Filed: Aug. 2, 1982

Related U.S. Application Data

[63] Continuation of Ser. No. 259,382, May 1, 1982, abandoned.

[51] Int. Cl.$^3$ ............... C07D 213/55; A01N 43/40
[52] U.S. Cl. .................................. 424/263; 546/341; 546/342
[58] Field of Search ............... 546/341, 342; 424/263

[56] References Cited

U.S. PATENT DOCUMENTS 4,093,622  6/1978  Henrick et al. ............ 546/342
4,348,400  9/1982  Wong ....................... 424/263

Primary Examiner—Alan L. Rotman
Attorney, Agent, or Firm—Joel G. Ackerman

[57] ABSTRACT

Compounds having the formula

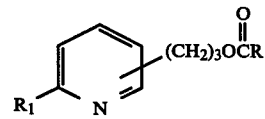

in which R is $C_3$–$C_5$ alkyl, $C_3$–$C_5$ alkenyl, cyclopropyl, or

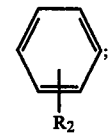

$R_1$ is $C_1$–$C_4$ alkyl; $R_2$ is $C_1$–$C_4$ alkyl, and the side chain is substituted on the pyridyl ring at the 2- or 3-position, are effective insect repellents.

27 Claims, No Drawings

INSECT REPELLENT COMPOUNDS

This is a continuation, of application Ser. No. 259,382, filed May 1, 1982 now abandoned.

This invention relates to novel compounds having the formula

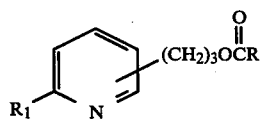

in which R is $C_3$–$C_5$ alkyl, $C_3$–$C_5$ alkenyl, cyclopropyl, or

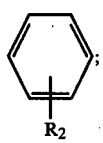

$R_1$ is $C_1$–$C_4$ alkyl; $R_2$ is $C_1$–$C_4$ alkyl, and the side chain is substituted on the pyridyl ring at the 2- or 3-position. The terms "alkyl" and "alkenyl" include both straight and branched-chain groups, for instance, methyl, ethyl, n-propyl, isopropyl, n-butyl, isobutyl, sec-butyl, tert-butyl, and various amyl groups; propenyl, allyl, 1-methyl-2-propenyl, 2-methyl-1-propenyl, and various pentenyl moieties. The compounds have utility as insect repellents, particularly for repelling flying insects from lighting and/or feeding.

The compounds of this type can be prepared by reaction of an appropriate pyridyl propanol with an appropriate acyl chloride;

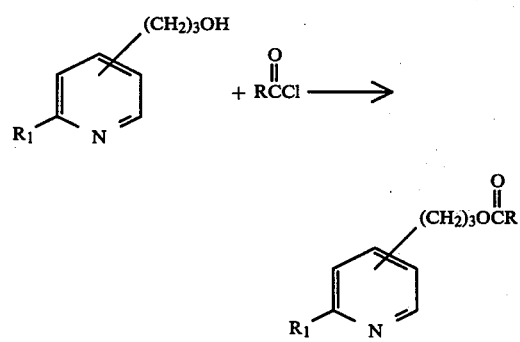

The 2-isomer of the pyridyl propanol in which $R_1$ is methyl, namely 6-methyl-pyridyl-2-propanol, is commercially available. The 3-isomer, if not commercially available, can be synthesized, for example, from 6-methyl-3-ethynyl pyridine,

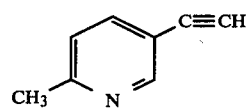

by the method of Umezawa et al., Japanese patent application No. 74/13180 (publication no.). Other starting materials, in which $R_1$ is $C_2$, $C_3$, or $C_4$ alkyl, can be similarly prepared.

The reaction is generally conducted at temperatures of about 0° C. to about 15° C. in the presence of a solvent such as methylene chloride and a hydrogen chloride acceptor such as triethylamine or pyridine. The product is recovered by conventional extraction, washing, and filtration steps.

Preparation of such compounds is illustrated by the following example.

Preparation of gamma-(6-methyl-2-pyridyl)propyl 3-methyl-2-butenoate (Compound 1 herein)

In a flask equipped with a stirrer were placed 5.0 g (0.033 mole) 3-(6-methyl-2-pyridyl)-1-propanol, 2.9 g (0.036 mole) pyridine and 50 ml methylene chloride. The resulting clear yellow solution was cooled to 0° C. There was then added 4.3 g (0.036 mole), 3,3-dimethylacryloyl chloride at a rate so as to maintain the temperature at 15° C. maximum. After addition was complete, the solution was stirred for 3 hours, with the temperature being permitted to rise to room temperature. The mixture was then washed with water and methylene chloride; the organic phase was separated, washed with 10% potassium carbonate solution, water, and a saturated sodium chloride solution, and dried over sodium sulfate. After drying, the material was filtered and the solvent stripped off to yield 7.6 g (98.4% of theoretical yield) of a light brown oil, $n_D^{30}$ 1.5085. The structure of the compound was confirmed by infrared (ir), nuclear magnetic resonance (nmr) and mass (ms) spectroscopy.

The following Table I contains a list of representative compounds of this invention.

TABLE I

| Compound No. | Substitution On Pyridine Ring | R | $R_1$ | $n_D^{30}$ |
|---|---|---|---|---|
| 1 | 2- | —CH=C(CH$_3$)$_2$ | CH$_3$ | 1.5085 |
| 2 | 2- | —CH$_2$—CH(CH$_3$)$_2$ | CH$_3$ | 1.4790 |
| 3 | 2- | —CH(CH$_3$)CH$_2$CH$_3$ | CH$_3$ | 1.4781 |
| 4 | 2- | (2-methylphenyl) | CH$_3$ | 1.5461 |
| 5 | 2- | (cyclopropyl) | CH$_3$ | 1.5033 |
| 6 | 2- | —C(CH$_3$)$_3$ | CH$_3$ | 1.4750 |
| 7 | 2- | —C(CH$_3$)=CH—CH$_3$ | CH$_3$ | 1.5027 |

The structures of the compounds in the foregoing Table I were confirmed by ir, nmr, and/or ms.

Insect Repellent Tests

The compounds described in the above Table I were tested for insect repellancy by the following procedures:

Mosquitos

A paper cup filled with pupae of the mosquito *Culex pipiens quinquefasciatus* (Say) was placed in a screened cage and the pupae allowed to emerge into adults. Sugar cubes were then saturated with 1.0 milliliter (ml.) of an acetone solution containing 0.1 wt.% of the test compound, and, for a control, with the same amount of acetone alone. After the cubes dried they were put into the screened cage. Repellency was determined by the number of mosquito adults lighting and feeding on the sugar cubes, with observations being made daily for 5 days after treatment. The number of days of complete repellency of mosquitoes from the sugar cubes was recorded.

Comparative tests were similarly conducted using the compound N,N-diethyl-m-toluamide, commercially manufactured and employed as an insect repellent, generally known by the generic name "deet". The results of the tests of deet and the compounds of Table I are shown in the following Table II. The numbers in each column represent the number of days of complete repellency observed using the specified concentration.

TABLE II

| Compound | Days Repelled, 0.1 wt. % |
|---|---|
| 1 | >5 |
| 2 | 2 |
| 3 | 2 |
| 4 | 2 |
| 5 | 4 |
| 6 | 1 |
| 7 | >5 |
| deet | 1 |
| control | 0 |

Houseflies:

The insect utilized for this test was the housefly, *Musca domestica* (L.). One hundred houseflies of mixed sexes were placed in test cages. In each cage was placed a sugar cube saturated with 1.0 ml of acetone containing 1 wt.% of the test compound. The cube was dried and weighed before being placed in the cage. Each cage also contained a water-saturated cotton plug, to provide moisture. The test cages were placed on a turntable and rotated at 1.5 revolutions per minute to keep the flies randomly distributed inside the cage. After 48 hours the flies in each cage were anesthetized with carbon dioxide. The sugar cubes were removed and reweighed and the percentage weight loss (due to consumption by the flies) recorded. A repellency ratio, calculated as the percent weight loss of the treated sugar cube divided by the percent weight loss of a control sugar cube treated with acetone only was calculated. The lower the repellency ratio, the greater the repellency of the test compound. The repellency ratios of the test compounds are shown in the following Table III. Values given for the repellency ratio represent an average of from one to three replications per compound.

TABLE III

| Compound | Repellency Ratios; Concentration, 1 wt. % |
|---|---|
| 1 | 0.36 |
| 2 | 0.43 |
| 3 | 0.42 |
| 4 | 0.48 |
| 5 | 0.46 |
| 6 | 0.36 |
| 7 | 0.36 |
| deet | 0.60 |

Thus at a concentration of 1% by weight, the test compounds repelled insects to the extent that the weight loss of sugar cubes treated with those compounds was less than 50% of that of the control (untreated) cubes.

The novel compounds of this invention may be used as insect repellents in either diluted or undiluted form. When used in a diluted form, the compounds may be embodied in compositions containing relatively high or relatively low concentrations of the active compound. For example, the active compound can be incorporated into relatively high concentration compositions such as wet sprays or solutions in alcohol or other suitable solvents. Such compositions may contain, in addition to the active compound, adjuvants such as emulsifying agents, surface active agents, anti-oxidants and propellants which may be found normally in insect repellent preparations. The active compounds of this invention may be employed as the sole active component of such compositions or may be used in admixture with other compounds having a similar or different utility. For example, the compounds may be incorporated into creams, lotions, powders, suntan oil, insecticides and other preparations which may contain pesiticidal or other useful substances, as well as into compositions of various types used for treating fabrics or articles of clothing to render them insect repellent. In general, compositions for repellent use may contain from 0.5 to up to 80 weight %, preferably from 2 to about 40 weight %, of the novel active compounds.

Examples of typical formulations employing compounds of this invention are for instance,

EXAMPLE 1: EMULSIFIABLE CONCENTRATE

| Component | Weight % |
|---|---|
| Compound 1 | 53.6 |
| Aromatic Hydrocarbon Solvent | 36.4 |
| Emulsifier | 10.0 |
| Total | 100.0 |

EXAMPLE 2: LOTION

| Component | Weight % |
|---|---|
| Compound 3 | 10.7 |
| Lanolin | 4.8 |
| Mineral oil | 8.0 |
| Trihydroxyethylamine stearate | 1.8 |
| Glycosterin | 0.8 |
| Glycerine | 4.6 |
| Sodium benzoate | 1.0 |
| Water | 68.3 |
| Total | 100.0 |

EXAMPLE 3: ALCOHOL SOLUTION

| Component | Weight % |
|---|---|
| Compound 4 | 53.6 |

-continued

| Component | Weight % |
| --- | --- |
| Isopropanol | 46.4 |
| Total | 100.0 |

EXAMPLE 4: ALCOHOL SOLUTIONS

| Component | Weight % |
| --- | --- |
| Compound 5 | 80.0 |
| Ethanol | 20.0 |
| Total | 100.0 |

EXAMPLE 5: WETTABLE POWDER

| Component | Weight % |
| --- | --- |
| Compound 7 | 26.9 |
| Hydrated calcium silicate | 62.1 |
| Sodium lignosulfonate | 5.0 |
| Orzan A (mixture of ammonium lignosulfonate and wood sugars) | 5.0 |
| Wetting agent | 1.0 |
| Total | 100.0 |

What is claimed is:

1. A compound having the formula

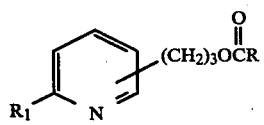

in which R is $C_3-C_5$ alkyl, $C_3-C_5$ alkenyl, or

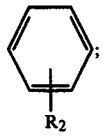

$R_1$ is $C_1-C_4$ alkyl; $R_2$ is $C_1-C_4$ alkyl; and the side chain is substituted on the pyridine ring at the 2- or 3-position.

2. A compound according to claim 1 in which the side chain is substituted on the pyridine ring at the 2-position.

3. A compound according to claim 1 in which the side chain is substituted on the pyridine ring at the 3-position.

4. A compound according to claim 1 in which R is $C_3-C_5$ alkyl.

5. A compound according to claim 1 in which R is $C_3-C_5$ alkenyl.

6. A compound according to claim 1 in which R is 2-methyl-1-propenyl, $R_1$ is methyl, and the side chain is substituted on the pyridine ring at the 2-position.

7. A compound according to claim 1 in which R is isobutyl, $R_1$ is methyl, and the side chain is substituted on the pyridine ring at the 2-position.

8. A compound according to claim 1 in which R is sec-butyl, $R_1$ is methyl, and the side chain is substituted on the pyridine ring at the 2-position.

9. A compound according to claim 1 in which R is o-tolyl, $R_1$ is methyl, and the side chain is substituted on the pyridine ring at the 2-position.

10. A compound according to claim 1 in which R is tert-butyl, $R_1$ is methyl, and the side chain is substituted on the pyridine ring at the 2-position.

11. A compound according to claim 1 in which R is 1-methyl-1-propenyl, $R_1$ is methyl, and the side chain is substituted on the pyridine ring at the 2-position.

12. A method of repelling but not killing insects from a locus to be protected therefrom, comprising applying to said locus an effective insect-repelling but non-lethal amount of a compound having the formula

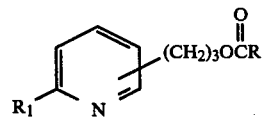

in which R is $C_3-C_5$ alkyl, $C_3-C_5$ alkenyl, or

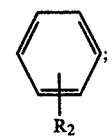

$R_1$ is $C_1-C_4$ alkyl; $R_2$ is $C_1-C_4$ alkyl; and the side chain is substituted on the pyridine ring at the 2- or 3-position.

13. A method according to claim 12 in which the compound is applied in an amount effective to repel mosquitoes.

14. A method according to claim 12 in which the compound is applied in an amount effective to repel houseflies.

15. A method according to claim 12 in which the side chain is substituted on the pyridine ring at the 2-position.

16. A method according to claim 12 in which the side chain is substituted on the pyridine ring at the 3-position.

17. A method according to claim 12 in which R is $C_3-C_5$ alkyl.

18. A method according to claim 12 in which R is $C_3-C_5$ alkenyl.

19. A method according to claim 12 in which R is 2-methyl-1-propenyl, $R_1$ is methyl, and the side chain is substituted on the pyridine ring at the 2-position.

20. A method according to claim 12 in which R is isobutyl, $R_1$ is methyl, and the side chain is substituted on the pyridine ring at the 2-position.

21. A method according to claim 12 in which R is sec-butyl, $R_1$ is methyl, and the side chain is substituted on the pyridine ring at the 2-position.

22. A method according to claim 12 in which R is o-tolyl, $R_1$ is methyl, and the side chain is substituted on the pyridine ring at the 2-position.

23. A method according to claim 12 in which R is tertbutyl, $R_1$ is methyl, and the side chain is substituted on the pyridine ring at the 2-position.

24. A method according to claim 12 in which R is 1-methyl-1-propenyl, $R_1$ is methyl, and the side chain is substituted on the pyridine ring at the 2-position.

25. An insect repellent composition containing an amount of a compound having the formula

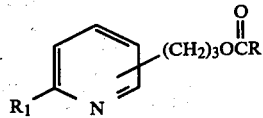

in which R is $C_3$–$C_5$ alkyl, $C_3$–$C_5$ alkenyl, or

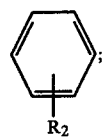

$R_1$ is $C_1$–$C_4$ alkyl; $R^2$ is $C_1$–$C_4$ alkyl; and the side chain is substituted on the pyridine ring on the 2- or 3-position, effective to repel insects; and an inert diluent or carrier.

26. A composition according to claim 25 containing an amount of the compound effective to repel mosquitoes.

27. A composition according to claim 25 containing an amount of the compound effective to repel houseflies.

* * * * *